United States Patent [19]

Relenyi

[11] Patent Number: 4,661,344

[45] Date of Patent: Apr. 28, 1987

[54] ANTIMICROBIAL CATION EXCHANGE COMPOSITION

[75] Inventor: Attila G. Relenyi, Midland, Mich.

[73] Assignee: The Dow Chemical Company, Midland, Mich.

[21] Appl. No.: 383,665

[22] Filed: Jun. 1, 1982

[51] Int. Cl.$^4$ .................... A61K 31/74; A01N 37/34
[52] U.S. Cl. ...................................... 424/79; 514/528
[58] Field of Search ........................................... 424/79

[56] References Cited

U.S. PATENT DOCUMENTS

| Re. 29,826 | 11/1978 | Konya et al. | 424/304 X |
|---|---|---|---|
| 2,366,007 | 12/1944 | D'Alelio | 424/DIG. 7 |
| 2,419,888 | 4/1947 | Nolan et al. | 167/38 |
| 2,977,313 | 3/1961 | Roland | 252/99 |
| 3,016,327 | 1/1962 | Schmitz et al. | 167/22 |
| 3,413,109 | 11/1968 | Vartiak | 71/65 |
| 3,493,658 | 2/1970 | Schmidt et al. | 424/304 |
| 3,761,238 | 9/1973 | Errede | 71/67 |
| 4,022,605 | 5/1977 | Konya et al. | 424/304 X |
| 4,076,622 | 2/1978 | Costin | 424/79 X |
| 4,145,304 | 3/1979 | Melnick et al. | 424/79 X |
| 4,174,277 | 11/1979 | Melnick et al. | 424/79 X |
| 4,221,778 | 9/1980 | Raghunathan | 424/79 X |
| 4,238,477 | 12/1980 | Lambert et al. | 424/79 |

OTHER PUBLICATIONS

Chemical Abstracts vol. 84: 169293t, (1976); Nieuwenhuys.
Chemical Abstracts vol. 82: 57322d, (1975); Thoma et al.
Merck Index; 8th Edition, (1968); p. 812.

Primary Examiner—Leonard Schenkman
Assistant Examiner—Joseph A. Lipovsky

[57] ABSTRACT

Antimicrobial cation exchange compositions comprising a cation exchange resin having absorbed thereon an antimicrobial chosen from the class consisting of halocyanoacetamide and 2-acylamino-2-halo alkyl acetate antimicrobials. Said compositions are useful as sustained release antimicrobial compositions. In addition, said compositions can be used to simultaneously remove cations and microbes from an aqueous solution.

14 Claims, No Drawings

ANTIMICROBIAL CATION EXCHANGE COMPOSITION

BACKGROUND OF THE INVENTION

This invention relates to antimicrobial cation exchange compositions, more particularly to slow release antimicrobial cation exchange resin compositions.

Halocyanoacetamides are well known as antimicrobials as disclosed in, for example, U.S. Pat. Nos. 2,419,888 to Nolan et al. and 3,493,658 to Schmidt et al. Said halocyanoacetamides and other antimicrobials are known to be degradable in water and other aqueous fluids and while this property is desirable from an ecological standpoint, it often requires that the antimicrobials in any system to be disinfected be periodically replenished. While this can be accomplished by intermittently introducing large amounts of these antimicrobials into the system, such a procedure is generally inefficient because much of the antimicrobial degrades without acting on the microbes. Therefore, the most effective use of these antimicrobials requires a system of continuously introducing the antimicrobial into the fluid to be disinfected. Such continuous introduction of halocyanoacetamides requires the use of metering or similar equipment. In larger systems the cost of said metering equipment is not especially burdensome, but in some small scale operations the cost of said metering equipment is often prohibitive.

Antimicrobials such as formaldehyde are often employed in conjunction with ion exchange resins, such as in water purification systems. In present systems, the removal of microbes and the removal of cations is accomplished in separate steps, requiring two sets of equipment and extra processing time. Moreover, antimicrobials such as formaldehyde do not degrade rapidly and are difficult to handle. It would be desirable to have a single process wherein both cations and microbes are simultaneously removed from an aqueous fluid, using a degradable, easily handled antimicrobial.

In view of the deficiencies of the known art, it would be desirable to have an inexpensive means for the continuous release of antimicrobials into a system to be disinfected. In addition, it would be desirable to provide a cation exchange resin having antimicrobial properties.

SUMMARY OF THE INVENTION

In one aspect, the present invention is an antimicrobial cation exchange composition comprising a strong acid type cation exchange resin and an antimicrobial which is reversibly attached to said cation exchange resin. Surprisingly, the antimicrobial cation exchange compositions of this invention slowly release the antimicrobial upon contact with water or a solvent for the antimicrobial, providing continuous introduction of active antimicrobials into the treated system. In addition, the antimicrobial cation exchange compositions of this invention retain the ion exchange characteristics of untreated cation exchange resins and will continue to exchange ions while simultaneously releasing antimicrobials into the system.

In another aspect, the present invention is a process for preparing an antimicrobial cation exchange composition comprising contacting a strong acid type cation exchange resin with an antimicrobial under conditions that the antimicrobial is reversibly attached to said cation exchange resin in an amount sufficient to impart antimicrobial activity to the cation exchange resin.

In still another aspect, the present invention is a method of continuously releasing antimicrobials into an aqueous fluid comprising continuously or intermittently contacting a microbe-containing aqueous fluid with an antimicrobial cation exchange composition of this invention.

In yet another aspect, this invention is a method of simultaneously removing microbes and cations from an aqueous fluid said method comprising contacting an aqueous fluid containing exchangeable cations and microbes with an antimicrobial exchange composition of this invention.

The antimicrobial cation exchange composition of the present invention afford an inexpensive means of continuously releasing antimicrobials into an aqueous fluid. Because the antimicrobial is released by the composition slowly upon contacting said composition with an aqueous fluid, no metering or other expensive equipment is needed. The antimicrobial cation exchange composition of this invention is simply placed in contact with the aqueous fluid and removed therefrom when the halocyanoacetamide content of the composition is sufficiently reduced such that effective levels of the antimicrobial are no longer released therefrom. The spent antimicrobial cation exchange composition can be then discarded or reloaded for future use. When the antimicrobial cation exchange composition of this invention is also employed to exchange cations, the spent composition can be regenerated and reloaded to provide a reusable composition.

DETAILED DESCRIPTION OF THE INVENTION

The antimicrobial cation exchange composition of this invention comprise a cation exchange resin and an antimicrobial which is reversibly attached to said cation exchange resin. Preferably, said antimicrobial contains an electrophilic group which reversibly interacts with the anionic groups on the cation exchange resin. Said electrophilic group is advantageously a carbonyl group, and the antimicrobial is most preferably one represented by the general structure

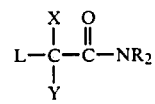

wherein each R is hydrogen or an alkyl group having from 1 to 10 carbon atoms, X is halogen, Y is hydrogen or halogen and L is an electron-withdrawing group. Exemplary electron-withdrawing groups include cyano, alkoxycarbonyl, nitro and like groups.

The compositions of this invention contain a quantity of antimicrobial sufficient to impart antimicrobial activity to the cation exchange resin, preferably from about 0.1 to 20 weight percent of antimicrobial based on the weight of the resin. While higher loading of the antimicrobial onto the resin is preferred, it is noted that even with relatively low loading, i.e., from about 0.1 to 2 weight percent, sufficient antimicrobial activity is imparted to the complex.

In a preferred embodiment, L is a cyano group, and the antimicrobial is a halocyanoacetamide as represented by the general formula:

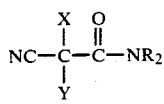

wherein X, Y and R are defined hereinabove. Preferably, each R is hydrogen. Y is preferably halogen and more preferably both X and Y are chlorine or bromine. Most preferably the halocyanoacetamide is 2,2-dibromo-2-nitrilopropionamide (DBNPA).

Also preferred as the antimicrobial of this invention are those 2-acylamino-2-halo alkyl acetate antimicrobials disclosed in my copending application Ser. No. 353,688, filed Mar. 1, 1982. Said antimicrobials are represented by the general structure:

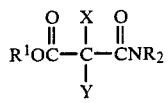

wherein $R^1$ is an alkyl group having from 1 to 10 carbon atoms and each R, X and Y are as described hereinabove. Preferably, X and Y are both bromine and the compound is 2-acetamino-2,2-dibromoethyl acetate.

The 2-acylamino-2-haloalkyl acetates suitably employed in this invention may be prepared by reacting a cyanoacetate ester represented by the generic formula:

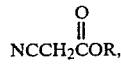

wherein R is $C_{1-10}$ alkyl with a halogen and water in a suitable organic solvent. Suitable solvents include carbon tetrachloride, acetonitrile, any saturated halogenated hydrocarbon and (poly)alkylene glycols. According to the process, the cyanoacetate ester is heated to an elevated temperature in the organic solvent. A sufficient amount of a halogen, selected from the group including bromine, chlorine, iodine and fluorine, preferably bromine, is added to the solution to provide at least two equivalents of halogen for each equivalent of cyanoacetate. Between one and two equivalents of water are co-added with the halogen over a period of between 3 and 10 hours or supplied in a mixture with one or more of the reactants or the solvent. Suitable temperatures for the addition of the halogen reactant are between about 20° C. and 100° C., preferably between about 50° C. and 70° C. Once the halogen has been added, the solution is cooled to room temperature (about 20° C.) and stirred for a sufficient time for a slurry to develop, usually about 60 hours. The desired product, the corresponding 2-acylamino-2-haloalkyl acetate ester is easily recovered by ordinary techniques such as filtration. The corresponding monohalogenated compounds can be prepared by the same process by reducing the amount of halogen added to one equivalent. This reaction proceeds smoothly at atmospheric pressure, but elevated pressures may be used.

While it is not intended to limit the invention to any particular theory, it is believed that the antimicrobial is absorbed by the cation exchange resin rather than adsorbed. It is theorized that the halocyanoacetamide or the 2-acylamino-2-halo alkyl acetate reacts with the cation exchange resin to form a complex represented by the following structure:

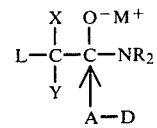

wherein D is the resin matrix, A represents an ion exchange site on the resin, M is the counterion and X, Y, R and L are as defined hereinbefore. ↑ represents an interaction between a cation exchange site on the resin and the carbonyl group on the antimicrobial, and is not intended to indicate the precise nature of said interaction.

Any cation exchange resin which is capable of absorbing the antimicrobial is suitably employed in the practice of this invention. In general, said cation exchange resins comprise a polymeric matrix to which is appended a plurality of ion exchange sites. The polymeric matrix can be a condensation polymer such as phenol/formaldehyde resin or may be a cross-linked addition polymer. Said addition polymers are generally copolymers of at least one $\alpha,\beta$-ethylenically unsaturated monomer and an ethylenically unsaturated monomer containing two or more nonconjugated terminal end groups. Illustrative of such monomers are those presented in *Polymer Processes*, edited by Calvin E. Schildknecht, published in 1956 by Interscience Publishers, Inc., New York, Chapter IV, "Polymerization in Emulsion" by H. Laverne Williams. In Table II on pages 122 and 123 thereof are listed diverse kinds of monomers which can polymerize alone or in mixtures to form water-insoluble polymer particles. Representative of such monomers are monovinylidene aromatics including styrene, vinyltoluene, ethyl vinyl benzene, $\alpha$-methyl styrene, chlorostyrene, bromostyrene, isopropylstyrene, dimethylstyrene, diethylstyrene and the like; alkyl esters of $\alpha,\beta$-ethylenically unsaturated carboxylic acids such as methylacrylate, methylmethacrylate and ethylacrylate; vinylaliphatic and alicyclic hydrocarbons such as 1,3-butadiene, 2-methylbutadiene, 3-dimethylbutadiene, cyclopentadiene; vinylidene compounds such as vinylidine chloride, vinyl alcohol, vinlyidene sulfate, mixtures thereof and the like. Representative cross-linking monomers or di- or polyvinylidene aromatics such as divinylbenzene or diallylphthalate, di- or polyacrylates such as 1,3-butylenediacrylate or ethylene glycol dimethacrylate, alkylmethacrylate and crotylmethacrylate and the like. In general, the polyvinylidene aromatics, particularly divinylbenzene, are preferably employed herein. Advantageously, the cross-linking monomer is employed in an amount from about 0.1 to about 25, preferably from about 0 to 10, weight percent based on the weight of the monomers employed in the preparation of the polymeric matrix. Various matrices of addition polymer commonly employed in commercial cation exchange resins include cross-linked monovinylidene aromatics such as styrene/divinylbenzene polymers, copolymers of acrylic acid or esters thereof with styrene or divinylbenzene and other vinyl addition polymers such as polyvinyl alcohol. Of these, the polystyrenes are preferred. Methods for the preparation of such polymers as granules or as spheroidal beads are well known in the art and reference is made thereto for the purpose of this invention.

Said methods are illustrated in *Ion Exchange* by F. Helfferich, published in 1962 by McGraw Hill Book Co., New York and U.S. Pat. Nos 2,366,007; 2,591,173; 2,597,437; 2,597,438; 2,614,085; 2,614,099; 2,518,420 and 3,549,562.

The polymeric matrix has affixed thereto a plurality of strong acid type anionic moieties. Representative anionic groups include sulfate, sulfonate, phosphate, phosphinate, arsenate and the like. Of these groups, sulfonate moieties are most preferred. Associated with the anionic groups is a counterion which is generally hydrogen, ammonium, an alkali metal or an alkaline earth metal.

Methods for introducing the ionic moiety to the polymer are well known and described, for example, in *Ion Exchange*, supra, the relevant portions of which are incorporated by reference.

Of the ion exchange resins advantageously employed in this invention, most preferred are sulfonated styrene/divinylbenzene copolymer resins such as described in U.S. Pat. Nos. 2,597,438; 3,252,921 and 3,549,562. All of the commonly available sulfonated styrene/divinylbenzene copolymer cation exchange resins are suitably employed in the practice of this invention. Commercially available sulfonated styrene/divinylbenzene copolymer resins include the so-called "macroporous" and "gel" type resins, as well as varieties having various particle sizes, counterions and degrees of cross-linking.

The antimicrobial ion exchange compositions of this invention are prepared by contacting the cation exchange resin with the solution of the antimicrobial in a solvent therefore. The solvent can be any solvent which does not react with the cation exchange resin and in which the antimicrobial is soluble. Preferably, the solvent is miscible with water. Exemplary solvents include acetonitrile, ethylene glycol, tetraethylene glycol and polyethylene glycols having molecular weights in the range of from about 100 to about 5000. Most preferred is tetraethylene glycol. The solution advantageously contains from about 0.1 to 50, more preferably from 1 to 20, most preferably from 2.5 to about 20, weight percent of the antimicrobial.

The antimicrobial solution is contacted with the cation exchange resin at ambient conditions. The cation exchange resin is contacted with the antimicrobial solution for a time sufficient to provide the desired amount of absorption, usually from about 0.5 to 100, preferably from 1 to about 20, more preferably from 1 to about 10, most preferably from about 1 to about 5 hours. While the amount of antimicrobial absorbed by the cation exchange resin depends somewhat on the concentration of the antimicrobial solution, the solvent, the counterion on the resin and the amount of time the antimicrobial solution is contacted with the resin, in general the cation exchange resin will absorb from about 0.5 to 20 percent of its weight of the antimicrobial. It has been found that both the rate of absorbency of the antimicrobial by the cation exchange resin and the amount of antimicrobial absorbed are increased when water is present in the system. Water can be introduced into the system by adding water to the antimicrobial solution. The antimicrobial solution can beneficially contain from about 1 to about 50 weight percent water. Alternately, and preferably, the cation exchange resin is water-swellable and is swollen with water prior to contacting said resin with the antimicrobial solution.

The antimicrobial cation exchange compositions thus formed are dried and packaged or otherwise prepared for end use.

Because the antimicrobial is released slowly by the compositions of this invention, said compositions can be employed to continuously disinfect aqueous fluids for an extended period of time. Microbe-containing fluids are disinfected with the compositions of this invention by contacting said aqueous fluids with the composition of this invention under conditions such that an effective amount of the antimicrobial is released into the fluid. The amount of fluid to be disinfected, the amount of the antimicrobial cation exchange composition employed, and the amount of the antimicrobial loaded onto the composition all affect the rate at which the antimicrobial is released into the fluid and are chosen such that the microbes in the fluid are effectively removed. The aqueous fluid may be treated by causing said fluid to flow over the composition, in which case the flow rate is such that the treated fluid contains an effective amount of the antimicrobial. In general, the antimicrobials employed in this invention are effective in amounts in the range from 0.5 to about 100 parts by weight per million parts of the treated fluid.

The rate of release of the antimicrobial from the antimicrobial cation exchange composition can be increased by decreasing the pH of the aqueous fluid contacted therewith. Thus, controlled release of the antimicrobial can be affected by changing the pH of the aqueous fluid to be treated. In general, the antimicrobial cation exchange compositions of this invention are effective when the pH of the aqueous fluid is in the range from 1 to about 9, preferably from 2 to 7. At a pH above about 9, many antimicrobials will rapidly degrade and the use of these antimicrobial cation exchange compositions under strongly basic conditions is therefore not preferred.

The compositions of this invention can be used to simultaneously remove cations and microbes from aqueous fluids by contacting aqueous fluids containing both cations and microbes with the composition of this invention in the manner described hereinbefore. When the compositions of this invention are employed to exchange ions as well as to disinfect, the composition will require regeneration periodically to retain its effectiveness as an ion exchanger. An important advantage of these compositions is that they can be regenerated and reloaded with antimicrobials simultaneously by contacting the compositions with a regeneration agent and then contacting the regenerated composition with a solution of the antimicrobial as described hereinbefore. Typically, an inorganic acid such as hydrochloric acid or sulfuric acid is used to regenerate cation exchange resins to the hydrogen form. Sodium chloride is most often used to regenerate cation exchange resin to their sodium form. Said regenerating agent is employed in the antimicrobial solution in amounts typically employed in the regeneration of previously known cation exchange resins. Inorganic acids are employed in an amount that is preferably in the range from about 0.2 to 20 percent by weight of the antimicrobial solution. Sodium chloride is advantageously employed in the range of about 2 to about 37 percent by weight of the antimicrobial solution.

One application of these antimicrobial cation exchange compositions is in treating aqueous cooling and heating systems. In such systems, microbes, fungi and the like often grow on the internal surfaces of the tubes and pipes of the system, which growth adversely affects the rate of heat transfer between the heating or cooling medium and the surrounding air. The use of metering equipment to continuously add antimicrobials to such systems is often prohibitively expensive in view of the total cost of the system, difficult to conform to the design requirements of the system or otherwise impracticable. The antimicrobial cation exchange composition of this invention can be readily inserted into the heating or cooling apparatus and replaced periodically to obtain continuous antimicrobial activity. Advantageously, the composition is inserted into the system as a packet or as a replaceable unit of the cooling system which can be readily removed and replaced as needed.

Another application of these compositions is in microemulsion flooding processes for secondary oil recovery as a biocidal water softening composition. In microemulsion flooding, a surfactant-stabilized dispersion of water and hydrocarbon is pumped into injection wells which surround the production well. The emulsion frees the crude oil trapped in subterranean deposits. The crude oil becomes suspended in the water and the emulsion is thickened with various synthetic or natural polymers such as xanthan gums. However, the xanthan gum is degraded by bacteria present in the water, and hardness in the water tends to deposit in the wells as calcium deposits. Accordingly, the water requires treatment prior to the flooding operation to remove hardness and bacteria. Present processes use ion exchange resins to remove the calcium and magnesium ions in the water and separately employ formaldehyde to kill bacteria. The antimicrobial cation exchange compositions of the present invention can be substituted for the cation exchange resin and the formaldehyde of these conventional present processes yielding comparable antimicrobial and softening activity in a single process step. Use of the antimicrobial cation exchange compositions of the present invention has the further advantage of employing degradable antimicrobials and significantly increasing the ease of handling of the antimicrobial. The antimicrobial compositions are employed in microemulsion flooding applications by contacting the flood water with the composition in the same manner as the water is contacted with the cation exchange resin in previous processes. Regeneration of the cation exchange composition and reloading of the antimicrobial onto the composition can be performed simultaneously by treating the composition consecutively with a regenerating agent and a solution of the antimicrobial. Said regeneration and reloading can be accomplished in an amount of time comparable to the time required for regeneration of conventional cation exchange resins.

The following examples are provided to illustrate the present invention and are not intended to limit the scope thereof. All parts and percentages are by weight unless otherwise noted.

EXAMPLE 1

Antimicrobial cation exchange composition (AMCEC) Sample Nos. 1-A and 1-B are prepared by contacting (a) 113.5 grams of a water-swollen macroporous sulfonated 20 percent cross-linked styrene divinylbenzene cation exchange resin in the acid form containing about 50 weight percent water with (b) 100 grams of a solution of 5 weight percent dibromonitrilopropionamide (DBNPA) in tetraethylene glycol (TEG).

In Sample No. 1-A, the cation exchange resin is contacted with the DBNPA solution for 37 minutes. The cation exchange resin in Sample No. 1-B is contacted with the DBNPA solution for 8 days. At the end of the contact period, the DBNPA solution is separated from each resin and diluted to 100 times its volume with water. The amount of DBNPA remaining in the diluted solution is measured by high performance liquid chromatography (HPLC). The decanted DBNPA solution from Sample No. 1-A contains 3.77 grams DBNPA, indicating that 1.3 grams of the antimicrobial are absorbed by the resin. In Sample No. 1-B, 1.6 grams of the antimicrobial are absorbed by the resin.

HPLC analysis in this and all the following examples is performed using a Whatman Partisil 10/25 ODS 25 cm column maintained at 45° C. and a Perkin Elmer LC 75 detector set at 214 nm. The eluent is a solution of 10 percent acetonitrile and 90 percent water buffered with phosphoric acid to a pH of 2.3. The eluent is pumped at a rate of 1.5 ml per minute using a 5000 psi pump equipped with a 35 foot flat tube pulse damper.

EXAMPLE 2

AMCEC Sample Nos. 2-A and 2-B are prepared using a water-swollen, microporous sulfonated 4 percent cross-linked styrene divinylbenzene cation exchange resin in the acid form. The resin is contacted with 100 grams of a 5 weight percent DBNPA solution as described in Example 1.

In Sample No. 2-A, the resin is contacted with the antimicrobial solution for 37 minutes. The amount of DBNPA removed from the solution is measured by HPLC as described in Example 1. In AMCEC Sample No. 2-A, 1.8 grams of the DBNPA are absorbed by the resin (36 percent of the DBNPA originally in the solution). In Sample No. 2-B, the resin is contacted with the DBNPA solution for 8 days and 4.2 grams of DBNPA are absorbed by the resin.

EXAMPLE 3

Sample Nos. 3-A and 3-B are prepared according to the method of Example 2, this time employing a solution containing 20 weight percent of DBNPA and 80 weight percent tetraethylene glycol. In Sample No. 3-A, the resin is contacted with the solution for 42 minutes and absorbs 4.7 grams of the antimicrobial. In Sample No. 3-B, the resin is contacted with the antimicrobial solution for 8 days and absorbs 18.7 grams of DBNPA.

EXAMPLES 4-7

Examples 4-7 illustrate the formation of antimicrobial cation exchange compositions using the sodium form of a dehydrated microporous sulfonated 8 percent cross-linked styrene DVB cation exchange resin.

Sample No. 4 is prepared by contacting 454 grams of the resin with 200 grams of a 10 weight percent solution of DBNPA in acetonitrile. After 45 hours, the resin is filtered and the filtrate diluted to 250 ml with acetonitrile and analyzed for DBNPA using HPLC as described in Example 1. The HPLC analysis shows that 10.88 grams (54.4 percent of the DBNPA initially in solution) are absorbed by the cation exchange resin.

Sample No. 5 is prepared by contacting 454 grams of the resin with 200 grams of a solution containing 20 grams of DBNPA, 90 grams of tetraethylene glycol and 90 grams of water. After 32 hours, the resin is filtered and the filtrate is analyzed for DBNPA as described in Example 1 above. The resin has absorbed 13.4 grams of DBNPA (67.0 percent of the available DBNPA).

Sample Nos. 6-A, 6-B, 6-C and 6-D are prepared by contacting 227 grams of the resin with 100 grams of a solution containing 2.5 weight percent DBNPA, 5 weight percent water and 92.5 weight percent tetraethylene glycol. Sample No. 6-A is contacted with the DBNPA solution for 1 hour, Sample No. 6-B for 1.5 hours, Sample No. 6-C for 2.5 hours and Sample No. 6-D for 48 hours. The amounts of DBNPA absorbed by these resins is determined according to the procedures described in Example 1 and are as shown in Table I below.

TABLE I

| Sample No. | Contact Time (hr) | DBNPA Absorbed (g) | % of Available DBNPA Absorbed |
|---|---|---|---|
| 6-A | 1 | 1.2 | 48 |
| 6-B | 1.5 | 1.3 | 52 |
| 6-C | 2.5 | 1.5 | 60 |
| 6-D | 48 | 1.38 | 55.2 |

Sample No. 7 is prepared by contacting for 1 hour, 227 grams of the resin with 100 grams of a solution containing 10 grams of DBNPA, 20 grams of water and 70 grams of tetraethyl glycol. The amount of DBNPA absorbed is determined by the method described in Example 1 to be 5.7 grams.

EXAMPLE 8

AMCEC Sample No. 4 is washed twice with 2 100-ml portions of hot acetonitrile for a period of 10 minutes per wash. The wash solvent is then analyzed for DBNPA using the HPLC techniques described in Example 1. The washing removes 0.20 gram of DBNPA, or only 1.83 weight percent of the DBNPA initially in the composition.

AMCEC Sample No. 5 is washed twice with 100-ml portions of hot acetonitrile for a period of 10 minutes per wash. The wash solvent is then analyzed for DBNPA and found to contain 0.66 gram of DBNPA or 4.96 weight percent of the DBNPA initially in the composition.

It is seen from this example that the absorbed antimicrobial is not rapidly removed from the AMCEC even when a good solvent for the antimicrobial is employed.

EXAMPLE 9

The AMCEC of Example 4 is tested for ion exchange capacity as follows: a 25-ml portion of the composition is placed into a beaker and converted to the hydrogen form by treating with about 500 ml of a 5 weight percent solution of hydrochloric acid for 30 minutes. The acid solution is then filtered from the treated composition and the composition is washed with water until the wash is neutral. To the washed resin is added sufficient water to form an aqueous slurry and to the slurry is added 25 ml of 1.0N sodium hydroxide. The resin is filtered and the filtrate titrated with 1 molar hydrochloric acid. A 5.8-ml portion of hydrochloric acid is required to neutralize the filtrate indicating that 19.2 millimoles of sodium hydroxide are consumed by the composition. The ion exchange capacity of the composition is then calculated to be 2.34 millimoles of sodium hydroxide per milliliter of composition.

The AMCEC of Example 5 is then tested in like manner and the ion exchange capacity of said composition is determined to be 2.25 milliequivalents of sodium per milliliter of composition. By comparison, a 25-ml sample of untreated resin has an ion exchange capacity of 2.09 milliequivalents of sodium per milliliter of resin. The above results show that the antimicrobial cation exchange compositions of this invention retain the ion exchange capacity of the cation exchange resins from which they are produced.

EXAMPLE 10

The bactericidal properties of AMCEC Sample Nos. 10-A to 10-D and 10-0 are demonstrated in this example. In all samples, the composition is prepared from a microporous, sulfonated 8 percent cross-linked styrene divinylbenzene cation exchange resin in the sodium form. The amount of antimicrobial (DBNPA in all cases) in the composition is expressed as a percentage based on the weight of the ion exchange resin.

The agar cup test method is used to determine the bactericidal properties of the compositions. A seeded agar plate is prepared by melting a quantity of agar and seeding the melted agar with a suspension of Enterobacter aerogenes (ATCC No. 13048). The seeded agar is then poured into a Petrie dish and allowed to harden. A circular plug 5 mm in diameter is then removed from the hardened agar to form a cup in the agar plate. Into the cup is placed, without contaminating the surrounding agar, 0.06 gram of the sample to be tested. The agar plate is then incubated at 30° C. for 24 hours and the growth of bacteria on the plate is visually observed. The diameter of the area of agar proximate to the cup area where the sample has been placed, in which no bacterial growth is seen, is measured as the zone of inhibition.

Sample Nos. 10-A to 10-D and Comparative Sample 10-0 are tested in this manner with the amount of DBNPA in the sample as well as the diameter of the zone of ihhibition as noted in Table II following.

TABLE II

| Sample No. | % DBNPA (1) | Diameter of Zone of Inhibition (cm) |
|---|---|---|
| 10-0* | 0 | 0 |
| 10-A | 7.3 | 3.1 |
| 10-B | 3.0 | 2.5 |
| 10-C | 1.4 | 2.1 |
| 10-D | 0.7 | 1.6 |

*Not an example of this invention.
(1) The amount of DBNPA in the composition sample expressed as a percentage of the weight of cation exchange resin in the composition.

It is seen from the above results that the compositions of this invention are effective antimicrobial compositions.

EXAMPLE 11

The effective leaching of the antimicorobial from the compositions of this invention is illustrated in this example. Sample Nos. 11-A through 11-D are compositions prepared from a microporous sulfonated 8 percent cross-linked styrene/divinylbenzene cation exchange resin in the sodium form having absorbed thereon 7.3 weight percent, based on the weight of the resin of DBNPA.

Sample No. 11-B is leached with diethyl ether in a Soxhlet extracter, using 20.0 g of the sample and 200 ml diethyl ether. After 24 hours of continuous extraction, 28.62 percent of the DBNPA originally on the cation exchange resin has been extracted by the ether. The ether is then replaced with fresh ether, and an additional 24 hours of extraction removes no more DBNPA.

Sample Nos. 11-C and 11-D are leached by placing 20 g of the sample into 200 ml of water at the pH indicated in Table III following. The water is filtered off at 2–3 hour intervals and replaced with fresh water. The total leach time for Sample Nos. 11-C and 11-D are each 16 hours.

The leached Sample Nos. 11-B through 11-D and Sample No. 11-A are tested for antibacterial properties according to the agar cup test procedure described in Example 10 with the results as indicated in Table III.

TABLE III

| Composition Sample No. (1) | Solvent | Leach Time | pH | Diameter of Zone of Inhibition (cm) |
|---|---|---|---|---|
| 11-A | None | — | 7.0 | 4.4 |
| 11-B | Ether | 2 days | 7.0 | 3.1 |
| 11-C | Water | 16 hours | 5.0 (2) | 1.6 |
| 11-D | Water | 16 hours | 10.0 (3) | 0 |

(1) All samples are a microporous sulfonated 8 percent cross-linked styrene divinylbenzene resin in Na$^+$ form containing, prior to leaching, 7.3 weight percent DBNPA, based on the weight of the resin.
(2) The pH is adjusted with a commercial buffer solution to 5.0
(3) The pH is adjusted with a commercial buffer solution to 10.0

The zones of inhibition of Sample Nos. 11-B and 11-C, as compared with that of Sample No. 11-A show that the antimicrobials in the compositions of this invention leach out when the composition is contacted with water or other solvents for the DBNPA but that the rate of the leaching is sufficiently slow such that after 2 days of exposure to water or ether, the composition still exhibits substantial antimicrobial activity. Sample No. 11-D shows no residual antimicrobial effect after 2 days of leaching with water at pH of 10.0. However, this effect is believed due to the degradation of the DBNPA in the basic media rather than complete leaching of the DBNPA from the composition.

EXAMPLE 12

The release of DBNPA into a flowing water stream by an AMCEC containing 8.84 weight percent DBNPA, based on the weight of the cation exchange resin, is illustrated in this example. The cation exchange resin in this example is the same as that employed in Example 10. A 33.9-g sample of the AMCEC is placed into a cartridge such that the AMCEC is retained therein while water is flowed therethrough. Deionized water is flowed through the cartridge at the rate of about 30 ml/minute (1.8 l/hr). The water so treated is not recycled. At ½ hour intervals, the treated water is analyzed for DBNPA. For the first 10 hours of operation, the treated water contains an average of 20 parts per million of DBNPA, which is an effective amount of DBNPA. After 10 hours of operation, the treated water contains less than 2 ppm DBNPA.

What is claimed is:

1. An antimicrobial cation exchange composition comprising a strong acid type cation exchange resin and an antimicrobially effective amount of an antimicrobial which is reversibly attached to said cation exchange resin, said antimicrobial being represented by the structure

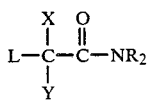

wherein X is halogen, Y is hydrogen or halogen, each R is independently hydrogen or an alkyl group having from 1 to 10 carbon atoms, and L is a cyano, alkoxycarbonyl or nitro group.

2. The composition of claim 1 wherein the antimicrobial is 2,2-dibromonitrilpropionamide.

3. The composition of claim 1 wherein the antimicrobial is 2-acylamino-2,2-dibromoethyl acetate.

4. The composition of claim 1 wherein said strong acid type cation exchange resin is a sulfonated resin.

5. The composition of claim 4 wherein such strong acid type cation exchange resin is sulfonated styrene divinylbenzene acid resin.

6. A method of slowly releasing an antimicrobial into an aqueous fluid over an extended period of time said method comprising contacting continuously or intermittently a microbe-containing aqueous fluid with a composition comprising a strong acid type cation exchange resin and an antimicrobially effective amount of an antimicrobial which is reversibly attached to said cation exchange resin, wherein the antimicrobial is represented by the structure

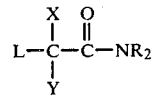

wherein X is halogen, Y is hydrogen or halogen, each R is independently hydrogen or an alkyl group having from 1 to 10 carbon atoms, and L is a cyano, alkoxycarbonyl or nitro group.

7. The method of claim 6 wherein the antimicrobial is 2,2-dibromonitrilopropionamide.

8. The method of claim 6 wherein the antimicrobial is 2-acylamino-2-halo alkyl acetate.

9. The method of claim 6 wherein the cation exchange resin is a sulfonated styrene divinylbenzene resin.

10. The method of claim 6 wherein the cation exchange resin is a polymer of an $\alpha,\beta$-unsaturated carboxylic acid or ester thereof.

11. A method of treating an aqueous fluid containing microbes and exchangable cations to remove said microbes and exchangable cations said method comprising contacting said aqueous fluid with a composition comprising a strong acid type cation exchange resin and an antimicrobially effective amount of an antimicrobial which is reversibly attached to said cation exchange resin wherein the antimicrobial is represented by the structure

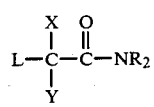

wherein X is halogen, Y is hydrogen or halogen, each R is independently hydrogen or an alkyl group having from 1 to 10 carbon atoms, and L is a cyano, alkoxycarbonyl or nitro group.

12. The method of claim 11 wherein said aqueous fluid contains calcium and magnesium ions.

13. The method of claim 11 wherein the antimicrobial is 2-acylamino-2-halo alkyl acetate.

14. The method of claim 11 wherein said antimicrobial is 2,2-dibromonitrilopropionamide.

* * * * *